(12) United States Patent
Norton et al.

(10) Patent No.: US 9,255,336 B2
(45) Date of Patent: Feb. 9, 2016

(54) METHOD AND APPARATUS FOR PRODUCING A STABILIZED ANTIMICROBIAL NON-TOXIC ELECTROLYZED SALINE SOLUTION EXHIBITING POTENTIAL AS A THERAPEUTIC

(71) Applicant: REOXCYN DISCOVERIES GROUP, INC., Salt Lake City, UT (US)

(72) Inventors: Verdis Norton, Sandy, UT (US); Gary L. Samuelson, Sandy, UT (US)

(*) Notice: Subject to any disclaimer, the term of this patent is extended or adjusted under 35 U.S.C. 154(b) by 176 days.

(21) Appl. No.: 13/727,191

(22) Filed: Dec. 28, 2012

(65) Prior Publication Data

US 2013/0092531 A1 Apr. 18, 2013

Related U.S. Application Data

(60) Division of application No. 12/383,212, filed on Mar. 20, 2009, now Pat. No. 8,367,120, which is a continuation-in-part of application No. 12/290,398, filed on Oct. 30, 2008, now abandoned.

(60) Provisional application No. 61/001,010, filed on Oct. 30, 2007.

(51) Int. Cl.
*C25B 1/26* (2006.01)
*C25B 1/30* (2006.01)
(Continued)

(52) U.S. Cl.
CPC .............. *C25B 15/02* (2013.01); *A61K 33/00* (2013.01); *A61K 33/14* (2013.01); *A61K 33/20* (2013.01); *A61K 33/40* (2013.01); *A61K 45/06* (2013.01)

(58) Field of Classification Search
CPC ... A61K 2300/00; A61K 33/40; A61K 33/20; A61K 33/14; C25B 1/13; C25B 1/30; C25B 1/26; C25B 15/02
See application file for complete search history.

(56) References Cited

U.S. PATENT DOCUMENTS

| 1,029,580 A | 6/1912 | Bane |
| 1,200,165 A | 10/1916 | Burgess |

(Continued)

FOREIGN PATENT DOCUMENTS

| EP | 03050466 | 1/1990 |
| EP | 2078700 | 7/2009 |

(Continued)

OTHER PUBLICATIONS

Center for Biofilm Engineering, Proceedings Winter 2004, CBE Technical Advisory Conference, Feb. 5-6, 2004, Montana State University, Bozeman, Montana.

(Continued)

*Primary Examiner* — Abigail Fisher
*Assistant Examiner* — Jessica Kassa
(74) *Attorney, Agent, or Firm* — Dax D. Anderson; Kirton McConkie

(57) ABSTRACT

An improved method and apparatus for producing a stable, non-toxic, antimicrobial electrolyzed saline solution with a broad range of anti-infective and therapeutic applications. The resulting electrolyzed saline solution exhibits a marked lack of toxicity upon intravenous, aspired, oral or topical application in mammals for therapeutic applications providing a broad platform, including topical disinfection, antimicrobial application, wound treatment, oxidative stress reduction and enhancement of immune function to better detect malfunctioning cells.

18 Claims, 1 Drawing Sheet

(51) Int. Cl.
  *C25B 1/13*   (2006.01)
  *C25B 15/02*  (2006.01)
  *A61K 45/06*  (2006.01)
  *A61K 33/00*  (2006.01)
  *A61K 33/14*  (2006.01)
  *A61K 33/20*  (2006.01)
  *A61K 33/40*  (2006.01)

(56) References Cited

U.S. PATENT DOCUMENTS

| | | |
|---|---|---|
| 2,473,986 A | 6/1949 | Booth |
| 2,985,514 A | 5/1961 | Lundeen |
| 3,234,110 A | 2/1966 | Beer |
| 3,365,061 A | 1/1968 | Bray |
| 3,505,215 A | 4/1970 | Bray |
| 3,616,355 A | 10/1971 | Themy et al. |
| 3,622,479 A | 11/1971 | Schneider |
| 3,654,148 A | 4/1972 | Bradley |
| 3,749,524 A | 7/1973 | Jordan |
| 3,791,768 A | 2/1974 | Wanner |
| 3,825,122 A | 7/1974 | Taylor |
| 3,996,126 A | 12/1976 | Rasmussen |
| 4,000,065 A | 12/1976 | Ladha et al. |
| 4,019,986 A | 4/1977 | Burris et al. |
| 4,070,280 A | 1/1978 | Bray |
| 4,077,883 A | 3/1978 | Bray |
| 4,124,488 A | 11/1978 | Wilson |
| 4,138,210 A | 2/1979 | Avedissian |
| 4,151,092 A | 4/1979 | Grimm et al. |
| 4,187,173 A | 2/1980 | Keefer |
| 4,288,326 A | 9/1981 | Keefer |
| 4,290,873 A | 9/1981 | Weaver |
| 4,306,952 A | 12/1981 | Jansen |
| 4,367,140 A | 1/1983 | Wilson |
| 4,370,214 A * | 1/1983 | Kadija ............ 204/242 |
| 4,389,311 A | 6/1983 | La Freniere |
| 4,434,056 A | 2/1984 | Keefer |
| 4,534,713 A | 8/1985 | Wanner |
| 4,560,455 A | 12/1985 | Porta et al. |
| RE32,077 E | 2/1986 | deNora et al. |
| RE32,144 E | 5/1986 | Keefer |
| 4,613,415 A | 9/1986 | Wreath et al. |
| 4,632,754 A | 12/1986 | Wood |
| 4,710,233 A | 12/1987 | Hohmann et al. |
| 4,722,263 A | 2/1988 | Valentin |
| 4,756,830 A | 7/1988 | Fredkin |
| 4,759,844 A | 7/1988 | Lipschultz et al. |
| 4,761,208 A | 8/1988 | Gram et al. |
| 4,786,380 A | 11/1988 | van Duin et al. |
| RE33,135 E | 12/1989 | Wanner, Sr. et al. |
| 5,085,753 A | 2/1992 | Sherman |
| 5,207,916 A | 5/1993 | Goheen et al. |
| 5,221,451 A | 6/1993 | Seneff et al. |
| 5,244,579 A | 9/1993 | Horner et al. |
| 5,306,428 A | 4/1994 | Tonner |
| 5,316,740 A | 5/1994 | Baker et al. |
| 5,320,718 A | 6/1994 | Molter et al. |
| 5,334,383 A | 8/1994 | Morrow |
| 5,354,264 A | 10/1994 | Bae et al. |
| 5,358,635 A | 10/1994 | Frank et al. |
| 5,385,711 A | 1/1995 | Baker et al. |
| 5,496,466 A | 3/1996 | Gray |
| 5,503,736 A | 4/1996 | Schoenmeyr |
| 5,507,932 A | 4/1996 | Robinson |
| 5,531,887 A | 7/1996 | Miers |
| 5,534,145 A | 7/1996 | Platter et al. |
| 5,540,848 A | 7/1996 | Engelhard |
| 5,558,762 A | 9/1996 | Fife et al. |
| 5,560,816 A | 10/1996 | Robinson |
| 5,581,189 A | 12/1996 | Brenn |
| 5,597,482 A | 1/1997 | Melyon |
| 5,622,848 A | 4/1997 | Morrow |
| 5,674,537 A | 10/1997 | Morrow |
| 5,685,980 A | 11/1997 | Patapoff et al. |
| 5,725,758 A | 3/1998 | Chace et al. |
| 5,731,008 A | 3/1998 | Morrow |
| 5,753,098 A * | 5/1998 | Bess et al. ............ 205/501 |
| 5,928,490 A | 7/1999 | Sweeny |
| 5,958,229 A | 9/1999 | Filiopoulos et al. |
| 5,989,396 A | 11/1999 | Prasnikar et al. |
| 6,007,686 A | 12/1999 | Welch et al. |
| 6,056,666 A | 5/2000 | Williams |
| 6,106,691 A | 8/2000 | Nakamura et al. |
| 6,110,424 A | 8/2000 | Maiden et al. |
| 6,117,285 A | 9/2000 | Welch et al. |
| 6,261,464 B1 | 7/2001 | Herrington et al. |
| 6,309,523 B1 | 10/2001 | Prasnikar et al. |
| 6,426,066 B1 | 7/2002 | Najafi et al. |
| 6,514,401 B2 | 2/2003 | Chyou et al. |
| 6,524,475 B1 | 2/2003 | Herrington et al. |
| 6,632,336 B2 | 10/2003 | Kasuya |
| 6,632,347 B1 | 10/2003 | Buckley et al. |
| 6,736,966 B2 | 5/2004 | Herrington et al. |
| 6,964,739 B2 | 11/2005 | Boyd et al. |
| 7,008,523 B2 | 3/2006 | Herrington |
| 7,087,766 B2 | 8/2006 | Nagano et al. |
| 8,367,120 B1 | 2/2013 | Norton |
| 8,455,010 B1 | 6/2013 | Norton |
| 8,455,101 B2 | 6/2013 | Reese et al. |
| 2004/0195090 A1 | 10/2004 | Omasa |
| 2006/0039996 A1 | 2/2006 | Palmer |
| 2006/0076248 A1 | 4/2006 | Kindred |
| 2006/0137973 A1 | 6/2006 | Herrington |
| 2006/0157343 A1 | 7/2006 | Herrington |
| 2013/0095138 A1 | 4/2013 | Norton |
| 2013/0115307 A1 | 5/2013 | Norton |

FOREIGN PATENT DOCUMENTS

| | | |
|---|---|---|
| JP | 03065952 | 3/2003 |
| KR | 20020074262 | 9/2002 |
| WO | 83/00052 | 1/1983 |
| WO | 98/45503 | 10/1998 |
| WO | 01/10215 | 2/2001 |
| WO | 02/48054 | 6/2002 |

OTHER PUBLICATIONS

Dumont et al., Hydrogen peroxide-induced apoptosis is CD95-independent, requires the release of mitochondria-derived reactive oxygen species and the activation of NF-kappaB. Oncogene, 18(3): 747-757, abstract (1999).

Gomes et al., Fluorescence probes used for detection of reactive oxygen species. J. Biochem. Biophys. Methods, 65: 45-80 (2005).

Rabinovitch et al., Removal and inactivation of *Staphylococcus* epidermis biofilms by electrolysis. Applied and Environmental Microbiology, vol. 72, No. 9, pp. 6364-6366 (2006).

Renschler, M.F. The emerging role of reactive oxygen species in cancer therapy. European Journal of Cancer, 40:1934-1940 (2004).

\* cited by examiner

METHOD AND APPARATUS FOR PRODUCING A STABILIZED ANTIMICROBIAL NON-TOXIC ELECTROLYZED SALINE SOLUTION EXHIBITING POTENTIAL AS A THERAPEUTIC

RELATED APPLICATIONS

This application is a divisional application of U.S. patent application Ser. No. 12/383,212, filed Mar. 20, 2009, which is a Continuation-in-Part of U.S. patent application Ser. No. 12/290,398, filed Oct. 30, 2008, which claims priority to U.S. Provisional Patent Application Ser. No. 61/001,010, filed Oct. 30, 2007, the entire contents all of which are herein incorporated by reference in their entirety.

BACKGROUND OF THE INVENTION

1. Field

This invention pertains to an electrolytic method and apparatus for producing electrolyzed saline redox-balanced solutions. More particularly, it pertains to a method and apparatus used to produce a stable, non-toxic, antimicrobial electrolyzed saline redox-balanced solution from pure saline or hypertonic saline (NaCl and $H_2O$), both referred to hereafter as saline solution, exhibiting anti-infective and immune-enhancing potential as a therapeutic employing a balanced mixture of chemically reduced and oxidized species including Hypochlorous acid (HOCl), Hypochlorites ($OCl^-$, NaClO), dissolved Oxygen ($O_2$), Chlorine ($Cl_2$) and Hydrogen ($H_2$) gases, Hydrogen Peroxide ($H_2O_2$), Hydrogen ions ($H^+$), Hypochloride (ClO) and corresponding amounts of Superoxides ($*O_2^-$, $HO_2$), Ozone ($O_3$), Activated Hydrogen ions ($H^-$), Chloride ions ($Cl^-$), Hydroxides (NaOH, $OH^-$), Singlet Oxygen ($*O_2$) and other forms of Reactive Oxygen Species (ROS) ($*OCl$, $*HO^-$).

2. State of the Art

Electrolysis of saline solutions has long been used to produce antimicrobial solutions that are compatible with mammalian biology. Some examples include methods to produce chlorinated water, bleach and hydrogen peroxide. Typically, the methods and apparatus used to electrolyze these solutions employ ion-selective barriers between the electrodes in order to efficiently isolate the target molecules and eliminate unwanted byproducts. A fundamentally different method and apparatus for producing a non-toxic antimicrobial electrolyzed saline solution is disclosed in eight United States patents, and two Japanese patents and a Mexican patent based on these U.S. patents, all held by the applicant, covering various other applications for intravenous injected electrolyzed saline solution, the machinery that manufactures it, and the method by which it is manufactured. These U.S. patents are as follows:

U.S. Pat. No. 5,334,383, Morrow, dated Aug. 2, 1994 entitled "Electrically Hydrolyzed Salines as In Vivo Microbicides for Treatment of Cardiomyopathy and Multiple Sclerosis." This patent covers a method of treating antigen related infections related to cardiomyopathy and multiple sclerosis in humans and other warm blooded animals. It does not cover the substance itself, but covers a particular use of the substance. This method of treatment includes the use of an electrolyzed saline solution in conjunction with one or more modulating agents such as ascorbic acid (Vitamin C), with or without concurrent colchicine, to mimic or enhance the body's naturally occurring immune response to bacterial, viral or fungal infection.

U.S. Pat. No. 5,507,932, dated Apr. 16, 1996 entitled "Apparatus for Electrolyzing Fluids." This patent covers equipment that exposes a liquid solution to an electrical current, creating an electrolyzed solution. This equipment may be used to produce an electrolyzed saline solution, capable of killing bacterial, viral and fungal agents, for use in medical applications such as the treatment of antigen related infections in humans and other warm blooded animals. This patent covers the equipment used to produce the electrolyzed saline solution, not the substance itself.

U.S. Pat. No. 5,560,816, Robinson, dated Oct. 1, 1996 entitled "Method for Electrolyzing Fluids." This patent covers a method for electrolyzing fluids, by using specialized equipment to expose liquid solutions to an electrical current. Saline, for example, may be treated by this process to yield an electrolyzed saline solution, capable of killing bacterial, viral and fungal agents, for the treatment of antigen related infection in humans and other warm blooded animals. This patent covers the method by which the electrolyzed saline solution is produced, not the substance itself.

U.S. Pat. No. 5,622,848, Morrow, dated Apr. 22, 1997 entitled "Electrically Hydrolyzed Saline Solutions As Microbicides For In Vitro Treatment Of Contaminated Fluids Containing Blood." This patent covers a method of treating whole blood and other blood products with an electrolyzed saline solution to reduce infection with bacterial, viral and fungal agents. This patent covers a particular use of the electrolyzed saline solution, not substance itself.

U.S. Pat. No. 5,674,537, Morrow, dated Oct. 7, 1997 entitled "An Electrolyzed Saline Solution Containing Concentrated Amounts Of Ozone And Chlorine Species." This patent covers a specific electrolyzed saline solution containing a regulated amount of microbicidal agents including ozone and active chlorine species. This solution is intended for use in the treatment of infections in the body of humans and other warm blooded animals, or in blood or blood products. This patent covers the electrolyzed saline solution.

U.S. Pat. No. 5,731,008, Morrow, dated Mar. 24, 1998 entitled "Electrically Hydrolyzed Salines as Microbicides." This patent covers a method of using a specific electrolyzed saline solution containing a regulated amount of microbicidal agents including ozone and active chlorine species for the treatment of microbial infections, including HIV infection. The method includes intravenous administration of the solution along with one or more modulating agents such ascorbic acid (Vitamin C), with or without concurrent colchicine. This patent covers a method for using the electrolyzed saline solution, not the substance itself.

U.S. Pat. No. 6,007,686, Welch et al, dated Dec. 28, 1999 entitled "System for Electrolyzing Fluids for Use as Antimicrobial Agents." This patent covers a system for electrolyzing fluids, such as a saline solution, for use in sterilizing dental and medical instruments and other health care equipment. The patent covers the necessary equipment for generating and circulating the electrolyzed saline solution around the instruments to be sterilized, and includes specific claims for equipment designed for use with dental drill hand pieces and flexible tubing. This patent covers a process by which the electrolyzed saline solution may be made for a particular use, not the substance itself.

U.S. Pat. No. 6,117,285, Welch et al, dated Sep. 12, 2000 entitled "System for Carrying Out Sterilization of Equipment." This patent covers a system for cleaning and sterilizing medical and dental instruments to prevent the spread of infection from one patient to another. The covered system bathes the instrument in an electrolyzed saline solution and causes the solution to flow into and sterilize any openings in the equipment. It includes specific claims for systems designed specifically for the sterilization of dental drills and flexible tubing. This patent covers a particular use of the electrolyzed saline solution, not the substance itself.

Two Japanese and one Mexican patents provide corresponding coverage in those countries for several of the above U.S. patents. Applicants also have other pending applications with the US Patent and Trademark Office for patents on various treatment uses of the electrolyzed saline solution.

The above embodiments of these prior patents typically have produced measurably different variations of electrolyzed saline solution. Each variation, however, exhibited some antimicrobial action and many of these devices produced solutions with measurable amounts of the components (chlorine, pH, ozone, etc.) within the range of the disclosed regulated amounts. The resulting electrolyzed saline compositions, however, have not historically been satisfactorily consistent or controllable, specifically regarding the concentrations of Reactive Oxygen Species (ROS). In addition, these prior inventions could produce toxic chemicals (chlorates) in the process of electrolyzing the saline solution. Consequently, there is a need for an improved manufacturing method and apparatus, such as that described below, to consistently produce solutions suitable for therapeutic applications in humans and warm-blooded animals.

SUMMARY OF THE INVENTION

The improved method and apparatus described below provides an improved electrolyzing fluid containing regulated amounts of stable reactive oxygen species (ROS) particularly suited for stable, non-toxic antimicrobial applications and to aid the immune system in identifying and destroying malfunctioning cells. The invention comprises a method for making an electrolyzed saline solution for use as an in vivo treatment of a human or warm-blooded animal. Specifically, it comprises:

a. placing a saline solution having a saline concentration of at least about 0.15% within a container,
b. activating a fluid circulation device to maintain a flow of the saline solution between the electrode surfaces,
c. adjusting the temperature of the circulating saline at a preferred level to prevent production of chlorates and regulate the relative concentrations of resulting components,
d. placing in the saline solution an anode and a cathode associated with a power source, and
e. applying an effective voltage potential less than about thirty volts between the cathode and the anode sufficient to produce a balanced mixture of chemical redox balanced species including Hypochlorous acid (HOCl), Hypochlorites (OCl$^-$, NaClO), dissolved Oxygen (O$_2$), Chlorine (Cl$_2$) and Hydrogen (H$_2$) gases, Hydrogen Peroxide (H$_2$O$_2$), Hydrogen ions (H$^+$), Hypochloride (ClO) and corresponding amounts of Superoxides (*O$_2^-$, HO$_2$), Ozone (O$_3$), Activated Hydrogen ions (H$^-$), Chloride ions (Cl$^-$), Hydroxides (NaOH, OH$^-$), Singlet Oxygen (*O$_2$) and other forms of Reactive Oxygen Species (ROS) (*OCl, *HO$^-$) utilizing electron and proton donation, ion and dissolved gas transport to produce a specific redox balanced set of molecules and ions. This redox-balanced set of molecules and ions in combination are a potent anti-infective and help the immune system identify and destroy malfunctioning cells.

This electrolyzed saline solution is then administered to a human or warm-blooded animal for therapeutic use. Preferably, the electrolyzed saline solution is administered by injection, oral or anal ingestion, applied topically, used as a bath, applied in a wound dressing, or inhaled in atomized form.

The container for producing the electrolyzed saline solutions is fabricated from a biologically compatible material. In addition, the anode is made of a base metal selected from the group consisting of platinum, niobium, titanium or any metal compatible with platinum bonding with an outer layer of platinum bonded to the base metal. The shape of the anode has a cylindrical, or flat (planar) shaped structure. The anode is preferably permeable to fluid flow.

Usually the cathode is positioned coaxially or in parallel in relation to the anode. This cathode is made of a base metal selected from the group consisting of platinum, niobium, titanium or any metal compatible with platinum bonding with an outer layer of platinum bonded to the base metal and has a cylindrical, or flat (planar) shaped structure similar to that of the anode and is also preferably permeable to fluid flow.

The spacing between the surfaces of the cathode and the anode is typically not greater than about one inch. This invention has means to circulate and regulate the temperature of fluids during production, has appropriate electrode design and has methods that effectively stabilize the composition of the resulting solution.

The temperature, fluid flow and effective voltage are chosen as to eliminate production of chlorates and to create the desired mixture of components. These parameters are determined by experimentation. The resulting solution is consistently stable and suitable for in vivo therapeutic applications. The stable ROS concentration, for example, has a variation of less than 5% from batch to batch and from device to device when the same set of parameters are employed by each.

The effective voltage may be applied by direct current, alternating current, or various combinations of alternating current and direct current power sources, resulting in a combined effective voltage ranging anywhere between 0 and 30 volts. The effective voltage is chosen to eliminate the production of chlorates and to create the desired mixture of components containing stable ROS. For example, a typical temperature range of the saline solution is from 30 deg. F. to 100 deg. F. In the lower temperature range, less O$_2$ is absorbed by the fluid and the fluid has smaller electrical conductivity, therefore higher effective voltages can be utilized to maintain adequate electrical current required to provide regulated amounts of stable ROS without significantly increasing the probability of creating chlorates and while maintaining a pH of 7.2 to 7.5.

The effective voltage may be adjusted, as desired, to regulate the concentration of the components and the pH of the resulting solution over a large variety of temperatures and fluid flows. Wherein it is difficult to theoretically determine the concentrations of all the various resulting chemical components when given any specific set of parameters, the optimal effective voltage, fluid temperature and flow are determined by experimentation. This methodology allows for the intentional regulation of concentrations of the specific chemical components in these stable ROS enriched solutions, allowing for the optimization of solutions intended for specific purposes.

The method and apparatus thus provides a stable, ROS enriched, antimicrobial, non-toxic electrolyzed saline solutions with a specific redox-balanced set of molecules and ions in solution, hereinafter referred to as "electrolyzed saline solution" (ESS) that has the ability to attack infective microbes and enhances the ability of the immune system to recognize and destroy damaged or malfunctioning cells. An example of a preferred embodiment of the ESS solution is that produced by Reoxcyn Discoveries Group, Inc. of Sandy, Utah under the tradename "Reoxcyn™".

ESS solutions are balanced to normal and hypertonic saline and have been shown through extensive, repeatable research by accredited laboratories to be stable, nontoxic and exhibit remarkable antimicrobial, antiviral and therapeutic characteristics. Besides the therapeutic applications, the nature of these solutions also makes them suitable for applications in food safety, animal health, agriculture and sterilization. The ESS solutions exhibit a marked lack of toxicity upon intravenous, aspired, oral or topical application in mammals.

ESS solutions provide a broad platform for anti-infective and therapeutic applications covering several potential areas of use, including topical disinfection, antimicrobial application, wound treatment, oxidative stress reduction and enhancement of immune function. ESS solutions, being that they contain regulated amounts of stable reactive oxygen species (ROS), are particularly suited for enhancing the ability of the immune system to recognize and destroy damaged or malfunctioning cells. Such solutions can also be administered in a number of different ways appropriate for the desired therapeutic application.

Furthermore, all of the molecular components found in these solutions are involved in a growing field of scientific investigation categorized as redox messaging and regulation of genes. Such molecular components, being a balanced set of reduced species (RS) and reactive oxygen species (ROS), are the same molecules and ions that mirror those found in biological systems and are intimately involved in the ability of the immune system to recognize, detect, eliminate and heal infected, damaged or mutated tissues in mammals.

The measurement of concentrations of ROS inside the solutions has been done by means of a fluoro spectrometer, Nanodrop 3300, and three varieties of fluorescent dyes, R-Phycoerytherin (R-PE), Hydroxyphenyl fluorescein (HPF) and Aminophenyl fluorescein (APF), that are commonly used to determine relative ROS concentrations inside active biological systems and cells. The molecules in these dyes change shape, and therefore fluoresce only when exposed to molecular components in ROS. The resulting change in fluorescence can then be detected by the fluoro spectrometer and can be related to the concentration of ROS present. ROS concentrations in ESS solutions are verified and detected by either APF or R-PE fluorescent dyes, both of which produce entirely consistent measurements of relative concentrations of ROS in various concentrations and dilutions of ESS solutions. ROS measurements in ESS solutions have been linked using R-PE fluorescent dye, to the reaction of this dye to regulated concentrations of 2/2'-Axobis(2-methylpropionamide)dihidrochloride, a molecule that produces known amounts of ROS. This is not an absolute measurement, but it relates ROS in ESS to amounts of a known producer of ROS.

These fluorescent dyes are often used in combination with a fluorescence microscope to create high-resolution images of the build-up of ROS (oxidative stress) inside individual living cells. These dyes have been shown to specifically be sensitive to concentrations of ROS regardless of complex surrounding chemical environments.

Although APF and R-PE dyes are capable of measuring relative ROS concentrations in ESS solutions, no known absolute standard concentration for stabilized ROS in pure saline solutions exists. Furthermore, discrepancies in the decay time of these fluorescent dyes make measuring standardized amounts of ROS in other solutions incompatible with measuring those found in ESS. This may be due, in part, to the molecular complexes in ESS solutions that keep the ROS concentration stable, effectively shielding the free radicals from readily reacting with the dyes. The standard for ROS concentration in ESS solutions is therefore measured relative to the ROS concentration in a standardized solution that has been used in all of the antimicrobial and toxicity studies to date, both published and unpublished. Methods to measure absolute ROS concentrations in ESS solutions are actively being pursued.

The regulated amounts of ROS, thus measured, inside a variety of the ESS solutions produced by various embodiments of this invention have been shown to be stable, consistent and predictable, sufficient for therapeutic applications.

The method and apparatus thus produce a stable, non-toxic, antimicrobial electrolyzed saline solution with a broad range of anti-infective and therapeutic applications. The resulting electrolyzed saline solution is balanced to normal and hypertonic saline and has been shown to exhibit remarkable antimicrobial, antiviral and therapeutic characteristics. The nature of this electrolyzed saline solution makes it suitable for applications in food safety, animal health, agriculture and sterilization. These electrolyzed saline solutions also exhibit a marked lack of toxicity upon intravenous, aspired, oral or topical application in mammals. The therapeutic applications represent a broad platform, possibly covering a variety of potential areas of use, including topical disinfection, antimicrobial application, wound treatment, oxidative stress reduction and enhancement of immune function to better detect malfunctioning cells.

DESCRIPTION OF THE ILLUSTRATED EMBODIMENTS

Figure 1:
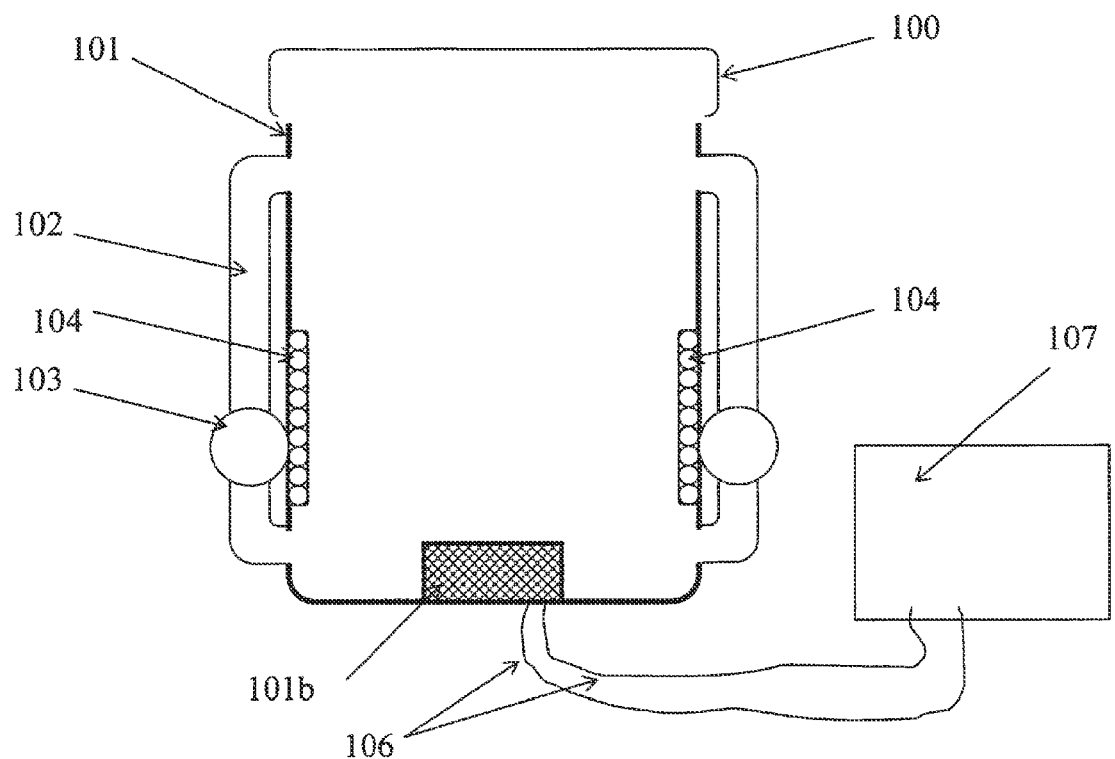
FIG. 1 is a side view of one preferred embodiment of the invention.

FIG. 1 is a side view of an embodiment of the invention. It has a container 101, which holds a saline solution having a saline concentration of at least about 0.15% to 1.0% by weight. The container may be fitted with a lid 100. The container 101 has a cylindrical anode 101a and a surrounding concentric cylindrical cathode 101b positioned on its bottom 105. The anode 101a and cathode 101b are operably associated with a power supply 107. The power supply 107 provides a source of electrical current with an effective voltage of under 30 volts via wires 106 affixed to the anode 101a and a cathode 101b.

The anode 101a is a mesh cylindrical ring comprised of titanium with an outer layer of platinum bonded to the titanium base. The cathode 101b is a cylindrical mesh ring comprised of titanium with an outer layer of platinum bonded to the titanium base that is positioned coaxially about the anode 101a. The spacing between the cathode 101b and the anode 101a, at the preferred flow rate below, is typically not greater than about one inch. Moreover, the effective voltage potential between the cathode 101b and the anode 101a is not greater than a preferred amount, typically under 30 volts.

A temperature regulation device, such as a combination heating/cooling device, is positioned along the sides 104 inside the container 101 to exchange heat with the saline solution in order to maintain the saline solution at a desired temperature between 30 deg. F. to 100 deg. F.

A circulation tube 102 is mounted on the exterior of the container 101 with openings connecting and in communication with the top and bottom interior of the container 101. The circulation tube 102 is associated with a fluid pump 103 to provide for fluid circulation and flow inside the container 101. This allows saline solution in the container 101 to flow through the anode 101a and cathode 101b assembly at a preferred flow rate, typically between 0.1 to 50 cc/cm$^2$/sec.

FIG. 1 also shows a second circulation tube 102 and fluid pump 103 similarly structured and mounted on the exterior of the opposite side of the container 101 that performs a similar fluid circulation function. This two tube 102 circulation structure and flow pattern insures complete mixing and electrolysis of the saline solution to produce ROS concentrations calculated to be between 0.05 and 50 ppm.

Figure 2:
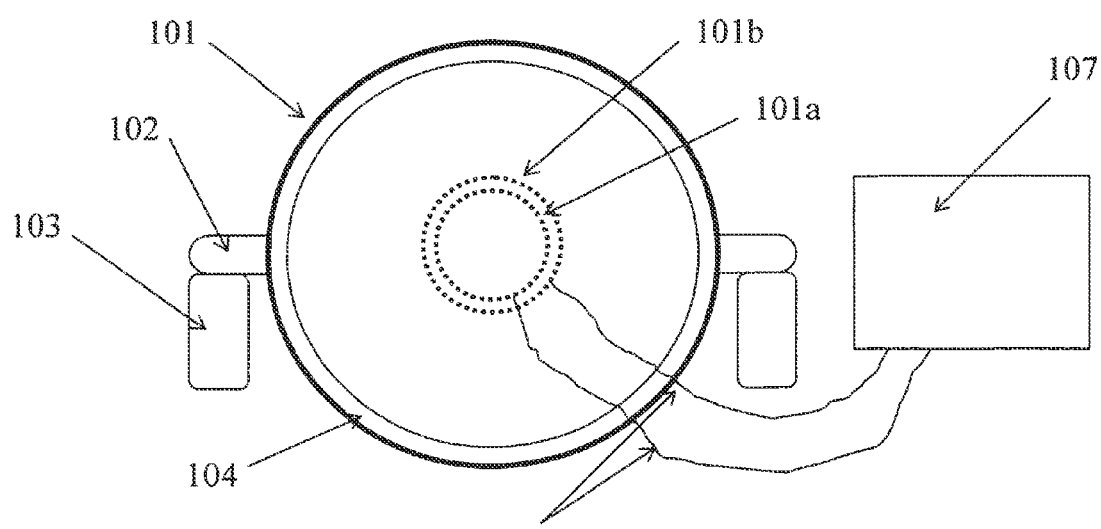
FIG. 2 is a top view of the preferred embodiment of the invention shown in FIG. 1.

FIG. 2 is a top view of the preferred embodiment of the invention shown in FIG. 1.

Although this reference has made reference to the illustrated embodiments, it is not intended to limit the scope of the claims. The claims themselves recite those features deemed essential to the invention.

We claim:

1. An apparatus for producing a stable, non-toxic, antimicrobial electrolyzed saline solution exhibiting anti-infective and immune-enhancing potential as a therapeutic containing regulated amounts of stable reactive oxygen species (ROS), comprising:
    a) a container filled with a saline solution having a saline concentration of at least about 0.15%, the container comprising a single exterior opening that is fitted with a lid;
    b) an inert anode and a spaced apart corresponding inert cathode placed within the saline solution;
    c) a combination heating/cooling device disposed coaxially along an interior side of the container configured to exchange heat with the saline solution to maintain the saline solution at a desired temperature between 30° F. and 100° F. to prevent production of chlorates and to regulate relative concentrations of resulting components during electrolysis;
    d) an exteriorly mounted circulation tube in fluid communication with a top and a bottom interior of the container configured with a pump to provide fluid circulation within the container to ensure complete mixing and electrolysis of the saline solution and a variation of less than 5% from batch to batch; and
    e) a power source associated with the anode and cathode to apply an effective voltage potential less than about thirty volts between the cathode and the anode sufficient to produce a balanced mixture comprising one or more of Hypochlorous acid (HOCl), Hypochlorites (OCl$^-$, NaClO), dissolved Oxygen (O$_2$), Chlorine (Cl$_2$) between 1 to 200 ppm, Hydrogen (H$_2$) gas, Hydrogen Peroxide (H$_2$O$_2$), Hydrogen ions (H$^+$), Hypochloride (ClO), Superoxides (*O$_2^-$, HO$_2$), Ozone (O$_3$) between about 1 ppm and about 50 ppm, Activated Hydrogen ions (H$^-$), Chloride ions (Cl$^-$), Hydroxides (NaOH, OH$^-$), Singlet Oxygen (*O$_2$), *OCl, and *HO$^-$, and wherein total ROS is between about 0.05 ppm and about 50 ppm, utilizing at least one of electron and proton donation, ion and dissolved-gas transport, the temperature, anode and cathode spacing, saline solution circulation rate, and effective voltage combination selected to achieve desired electrolysis efficiencies and stable specie compositions containing stable ROS compounds while preventing production of chlorates.

2. An apparatus for producing a stable, non-toxic, antimicrobial electrolyzed saline solution exhibiting anti-infective and immune-enhancing potential as a therapeutic containing regulated amounts of stable reactive oxygen species (ROS) according to claim 1, wherein the container is fabricated from a biologically compatible material.

3. An apparatus for producing a stable, non-toxic, antimicrobial electrolyzed saline solution exhibiting anti-infective and immune-enhancing potential as a therapeutic containing regulated amounts of stable reactive oxygen species (ROS) according to claim 1, wherein the anode is made of a base metal selected from the group consisting of platinum, niobium, titanium or any metal compatible with platinum bonding and is coated with an outer layer of platinum bonded to the base metal.

4. An apparatus for producing a stable, non-toxic, antimicrobial electrolyzed saline solution exhibiting anti-infective and immune-enhancing potential as a therapeutic containing regulated amounts of stable reactive oxygen species (ROS) according to claim 3, wherein the anode has a cylindrical, or flat (planar) shaped structure.

5. An apparatus for producing a stable, non-toxic, antimicrobial electrolyzed saline solution exhibiting anti-infective and immune-enhancing potential as a therapeutic containing regulated amounts of stable reactive oxygen species (ROS) according to claim 4, wherein the cathode has a cylindrical, or flat (planar) shaped structure and is positioned coaxially or in parallel in relation to the anode.

6. An apparatus for producing a stable, non-toxic, antimicrobial electrolyzed saline solution exhibiting anti-infective and immune-enhancing potential as a therapeutic containing regulated amounts of stable reactive oxygen species (ROS) according to claim 5, wherein the cathode is made of a base metal selected from the group consisting of platinum, niobium, titanium or any metal compatible with platinum bonding and is plated with an outer layer of platinum bonded to the base metal.

7. An apparatus for producing a stable, non-toxic, antimicrobial electrolyzed saline solution exhibiting anti-infective and immune-enhancing potential as a therapeutic containing regulated amounts of stable reactive oxygen species (ROS) according to claim 1, wherein the spacing between the cathode and the anode is less than one inch and is dependent upon ion transfer rates and electric fields to achieve desired electrolysis efficiencies to produce different varieties of solution components all containing stable ROS compounds.

8. An apparatus for producing a stable electrolyzed saline solution for treating a human or warm-blooded animal, comprising:
    a) a container filled with a saline solution having a concentration between about 0.15% and about 1.0% by weight, the container comprising a single exterior opening that is fitted with a lid;
    b) a permeable inert anode and a permeable inert cathode placed within the container associated with a power source configured to apply an effective voltage potential less than about thirty volts between the cathode and the anode to electrolyze the saline solution and produce a first target mixture of chemically reduced and oxidized molecules;

c) a combination heating/cooling device disposed coaxially along an interior side of the container configured to exchange heat with the saline solution to maintain the saline solution at a desired temperature between 30° F. and 100° F. during electrolysis to prevent production of chlorates and to regulate relative concentrations of resulting components during electrolysis; and d) two exteriorly mounted circulation tubes, each circulation tube in fluid communication with a top and a bottom interior of the container and configured with a pump to provide fluid circulation within the container, wherein the structure and flow pattern of the two exteriorly mounted circulation tubes ensure complete mixing and electrolysis of the saline solution to produce ROS concentrations between about 0.05 ppm and 50 ppm with a variation of less than 5% from batch to batch, wherein the first target mixture is configured to mirror a second target mixture of chemically reduced and oxidized molecules, the second target mixture corresponding to a biological system.

9. The apparatus of claim 8, wherein the first target mixture and the second target mixture are measured using a fluorospectrometer configured to measure concentrations of reactive oxygen species.

10. The apparatus of claim 9, wherein the concentrations are measured using at least one fluorescent dye selected from R-phycoerytherin, hydroxyphenyl fluorescein, and aminophenyl fluorescein.

11. The apparatus of claim 8, wherein the first target mixture of chemically reduced and oxidized molecules comprises one or more of $HOCl$, $OCl^-$, $NaClO$, $O_2$, $Cl_2$, $H_2$, $H_2O_2$, $H^+$, $ClO$, $*O_2-$, $HO_2$, $O_3$, $H^-$, $Cl^-$, $NaOH$, $OH^-$, $*O_2$, $*OCl$, or $*HO^-$.

12. The apparatus of claim 8, wherein the container is fabricated from a biologically compatible material.

13. The apparatus of claim 8, wherein the anode is made of a base metal selected from platinum, niobium, titanium, a combination thereof, or any metal compatible with platinum bonding and is coated with an outer layer of platinum.

14. The apparatus of claim 8, wherein the anode has a cylindrical or flat shaped structure.

15. The apparatus of claim 8, wherein the cathode has a cylindrical or flat shaped structure.

16. The apparatus of claim 8, wherein the cathode is made of a base metal selected from platinum, niobium, titanium, a combination thereof, or any metal compatible with platinum bonding, and is plated with an outer layer of platinum.

17. The apparatus of claim 8, wherein a space between the cathode and the anode is less than one inch.

18. The apparatus of claim 17, wherein the space is dependent upon ion transfer rates and electric fields.

* * * * *